United States Patent
Voice et al.

(10) Patent No.: US 7,153,698 B2
(45) Date of Patent: Dec. 26, 2006

(54) FIELD-DEPLOYABLE CARTRIDGE METHOD AND TEST KIT FOR ARSENIC

(75) Inventors: Thomas C. Voice, Okemos, MI (US); Ivan Havezov, Sofia (BG); Lisveth V. Flores del Pino, East Lansing, MI (US); David T. Long, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 733 days.

(21) Appl. No.: 10/616,138

(22) Filed: Jul. 9, 2003

(65) Prior Publication Data

US 2004/0101971 A1 May 27, 2004

Related U.S. Application Data

(60) Provisional application No. 60/395,028, filed on Jul. 11, 2002.

(51) Int. Cl.
*C02F 1/42* (2006.01)
*B01D 15/36* (2006.01)

(52) U.S. Cl. .................. 436/178; 210/263; 210/264; 210/660; 210/681; 210/688; 422/61

(58) Field of Classification Search ............. 210/263, 210/264, 660, 688; 436/178; 422/61
See application file for complete search history.

(56) References Cited

U.S. PATENT DOCUMENTS 4,814,148 A * 3/1989 Cheresnowsky et al. ...... 423/55

2001/0052495 A1* 12/2001 Friot ........................ 210/660
2003/0132155 A1* 7/2003 Litz et al. ................. 210/284

OTHER PUBLICATIONS

Nakazato et al., "Determination of arsenite, arsenate, and monomethylarsonic acid in seawater by ion-exclusion chromatography combined with inductively coupled plasma mass spectrometry using reaction cell and hydride generation techniques", Aug. 16, 2002, Elsevier Science, vol. 58, No. 1, pp. 121-132.*

* cited by examiner

*Primary Examiner*—Jill Warden
*Assistant Examiner*—Paul Hyun
(74) *Attorney, Agent, or Firm*—Ian C. McLeod; Steven E. Merritt (57) ABSTRACT

A method and test for field sample arsenic speciation in aqueous solutions, in particular, arsenic speciation in drinking water, is described. In particular, the method and test uses in series three columns wherein the first column removes interfering cations from water, the second column removes dimethylarsenate (DMA) from the water, and the third column removes As(V) (collectively $H_3AsO_4/H_2AsO_4^-/HAsO_4^{2-}/AsO_4^{3-}$) and monomethylarsinate (MMA) while As(III) (collectively $H_3AsO_3/H_2AsO_3^-/HAsO_3^{2-}/AsO_3^{3-}$) remains in the water effluent. The bound arsenic species are separately eluted from the columns in a laboratory and then each of the eluants and the effluent are tested for the arsenic species, preferably using graphite furnace atomic absorption spectroscopy.

36 Claims, 2 Drawing Sheets

FIELD-DEPLOYABLE CARTRIDGE METHOD AND TEST KIT FOR ARSENIC

CROSS-REFERENCE TO RELATED APPLICATION

This application claims priority to Provisional Patent Application No. 60/395,028, filed Jul. 11, 2002.

STATEMENT REGARDING FEDERALLY SPONSORED RESEARCH OR DEVELOPMENT

The research described herein was supported in part by Grant No. 5D43 TW00641-03 from the Fogarty International Center, National Institutes of Health. The U.S. Government has certain rights in the invention.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a method and test for field sample arsenic speciation in aqueous solutions, in particular, arsenic speciation in drinking water. In particular, the method and test uses in series three columns wherein the first column removes interfering cations from water, the second column removes dimethylarsenate (DMA) from the water, and the third column removes As(V) (collectively $H_3AsO_4/H_2AsO_4^-/HAsO_4^{2-}/AsO_4^{3-}$) and monomethylarsonate (MMA) while As(III) (collectively $H_3AsO_3/H_2AsO_3^-/HAsO_3^{2-}/AsO_3^{3-}$) remains in the water effluent. The bound arsenic species are separately eluted from the columns in a laboratory and then each of the eluants and the effluent are tested for the arsenic species, preferably using graphite furnace atomic absorption spectroscopy.

(2) Description of Related Art

Arsenic (As) contamination in natural waters is a worldwide problem that has become the subject of considerable international attention. Long-term ingestion of drinking water contaminated with arsenic has been associated with health problems including skin, bladder and lung cancers, skin lesions, cardiovascular effects, and anemia (Tseng et al., J. Nat. Cancer Inst., 1968. 40, 453–463; Wu et al., Am. J. Epidem., 1989, 130, 1123–1132; Chen and Wang, Cancer Res., 1990, 5, 5470–5474; Guo et al., Epidemiol., 1997, 8, 545–550; Hopenhayn-Rich et al., Intl. J. Epidemiol., 1998, 2, 561–569). Widespread health problems, including what is termed "blackfoot disease", have been observed in Bangladesh following a program to replace contaminated surface water supplies with shallow wells. Arsenic levels as high as 1820 µg/L have been reported in some wells in Taiwan (Tseng et al., J. Nat. Cancer Inst., 1968. 40, 453–463). Drinking water regulations for maximum allowable levels of arsenic vary by country across the range of 1 µg/L to 50 µg/L, the U.S. having recently lowered the standard to 10 µg/L (World Health Organization (WHO), Drinking Water Guidelines and Standard, 1996; Federal Register 66,14: 6976–7066). In most cases, the source of the arsenic is natural, resulting from the dissolution of arsenic-containing minerals in the aquifer (Kim et al., Environ. Sci. Technol., 2000, 34, 3094–3100; Simon, et al., Am. Mineral., 1999, 84, 1071–1079).

Investigations to date have focused largely on total arsenic levels in water supplies, but it is now understood that toxicity varies with the chemical form of the arsenic (National Research Council (NRC), Arsenic in Drinking Water. Washington: National Academy Press, 2001; Jain and Ali, Water Res., 2000, 34, 4304–4312). The common inorganic arsenic species in water include As(III) forms ($H_3AsO_3$, $H_2AsO_3^-$, $HAsO_3^{2-}$) and As(V) forms ($H_3AsO_4$, $H_2AsO_4^-$, $HAsO_4^{2-}$, $AsO_4^{3-}$) (Purnedu and Sharma, Water Res., 2002, 36, 4916–4926; Jeckel, In Arsenic in the Environment Part I; Nriagu, ED. John Wiley & Sons, New York, 1994, pp. 119–132). In addition, dissolved arsenic can occur as the organic forms dimethylarsinic acid/dimethylarsinate (($CH_3)_2AsO(OH)$) (DMAA/DMA), and monomethylarsonic acid/monomethylarsonate (($CH_3)AsO(OH)_2$) (MMAA/MMA). As(III) is reported to be 25 to 60 times as toxic as As(V) and several hundred times as toxic as methylated arsenicals (Korte and Fernando, Cri. Rev. Environ. Control, 1991, 21, 1–39). A number of other organic forms can be found, but these are generally considered to be non-toxic (Shiomi, In Arsenic in the Environment Part I; Nriagu, ED. John Wiley & Sons, New York, 1994, pp. 261–293; Philips, Aquat. Toxicol., 1990, 16, 151–186).

Total arsenic measurement in environmental matrices is relatively straightforward, with the principal methodologies based on flame (FAAS), hydride generation (HGAAS) or graphite furnace atomic absorption (GFAAS). Arsenic speciation has been more problematic and a number of separation techniques have been employed to resolve the various species. Separation approaches reported in the literature include methods based on sequential volatilization (Braman et al., Anal. Chem., 1977, 49, 621–625; Carvalho and Hercules, Anal. Chem., 1978, 50, 2030–2034; Heinrichs and Keltsch, Anal. Chem., 1982, 54, 1211–1214; Tesfalidet, S., Irgum, K. Anal. Chem., 1988, 60, 2031–2035; Galban et al., Spectr. Acta PartB-Atomic Spectr., 1993, 48, 53–63; Moller and Scholz, Anal. Proceedings, 1995, 32, 495–497; Frankenberger, Soil Biol. Biochem., 1998, 30, 269–274; Anderson et al., Analyst, 1986, 111, 1443; Lopez-Molinero et al., J. App. Spectr., 2001, 55, 1277–1282; Lopez-Molinero et al., Mikrochimica Acta, 1999, 131, 225–230), liquid-liquid extraction (Kalyanaraman and Khopkar, Talanta, 1977, 24, 63–65; Chakraborti et al., Anal. Chim. Acta, 1980, 120, 121–127; Puttermans et al., Anal. Chim. Acta, 1983, 149, 123–128; Bohr and Meckel, Fres. J. Anal. Chem., 1992, 342, 370–375), arsine generation (Narsito and Agterdenbos, Anal. Chim. Acta, 1987, 197, 315–321; Masscheleyn et al., Environ. Sci. Technol., 1991, 25, 1414–1419; Masscheleyn et al.,. Environ. Sci. Technol.,1991, 20, 96–100; Michel et al., Mikrochimica Acta, 1992, 109, 35–38; Howard and Comber, Mikrochimica Acta, 1992, 109, 27–33; Cabreros Pinillos et al., J. Anal. Chim. Acta, 1995, 300, 321–327; Burguera and Burguera, Talanta, 1997, 44, 1581–1604), ion exchange (Henry and Thorpe, Anal. Chem., 1980, 52, 80–83; Pacey and Ford, Talanta, 1981, 28, 935–938; Ficklin, Talanta, 1983, 30, 371–373; Aggett and Kadwani, Analyst, 1983, 108, 1495–1499; Gómez et al., Fres. J. Anal. Chem., 1997, 357, 844–849; Edwards et al., J.A.W.W.A,. 1998, 90, 104–113; Miller et al., Water Res., 2000, 34, 1397–1400; Le et al., Environ. Sci. Technol., 2000, 34, 2342–2347; Kim, Bull. Environ. Contam. Toxicol., 2001, 67, 46–51), ion-pair high-performance liquid chromatography (Grabinski, Anal. Chem., 1981, 53, 966–968; Ding et al., J. Chromat. A, 1995, 694, 425–432; Yalcin, Talanta, 1998, 47, 787–796; Le and Ma, Anal. Chem., 1998, 70, 1926–1933; Mattusch and Wennrich, Anal. Chem., 1998, 70, 3649–3655; Spuznar et al., Spectrochim. Acta B, 2000, 55, 779–793), and reversephase high-performance liquid chromatography (Brinckman et al., J. Chrom., 1980, 191, 31–46; Tye et al., Anal. Chim. Acta, 1985, 169, 195–200; Ebdon et al., Analyst, 1988, 113, 1159–1165; Bohari et al., Anal. Atomic Spec., 2001, 16, 774–778; Martin et al., J. Chrom.B: Biom. Appl., 1995, 66, 101–109; Le et al., Anal.Chem., 1996, 68, 4501–4506; Larsen, Spect. Acta Part B 1998, 53, 253–265; Londesborough et al., J. Fres. Anal. Chem., 1999, 363, 577–581).

The problem with using most of the above techniques to assess exposure to various arsenic species is that they are laboratory based and the distribution of species in a collected sample is not necessarily stable. For example, it has been shown that As(III) can be oxidized to As(V) during storage even when water samples preserved with hydrochloric acid and other chemicals (Borho and Wilderer, J. Water Supply Res. Technol.—Agua, 1997, 46, 138–143; Volke and Merkel, Acta Hydrochim., 1999, 27, 230–238). The arsenic separation methods reported in the literature that might be carried out on-site are limited to separation of As(III) and As(V) (Ficklin, Talanta, 1983, 30, 371–373; Edwards et al., J.A.W.W.A,. 1998, 90, 104–113; Kim, Bull. Environ. Contam. Toxicol., 2001, 67, 46–51; Russeva et al., Fres. J. Anal. Chem., 1993, 347, 320–323). Thus, there remains a need for a method capable of determining the distribution of the most toxic arsenic species (As(III), As(V), MMA, and DMA) at the point of exposure, at concentration levels of interest in drinking water.

Elevated arsenic concentrations are most frequently observed in groundwater supplies where it may exist as inorganic arsenate/arsenous acid (As(III)), or as arsenate/arsenic acids (As(V)). A number of organic forms can also be found in aquatic systems with monomethylarsonic acid ($(CH_3AsO(OH)_2$ or MMA) and dimethylarsinic acid ($(CH_3)_2AsO(OH)$ or DMA) being the most prevalent.

These different arsenic species exhibit significantly different toxicities: As(III) is reported to be 25 to 60 times as toxic as As(V) and several hundred times as toxic as methylated arsenicals (Kim et al., Environ. Sci. Technol., 2000, 34, 3094–3100). Therefore, a standard based only on total arsenic concentrations may actually represent a broad range of risk factors. These species also have different physical-chemical properties, which may require different water treatment strategies. Thus, while knowledge of total arsenic concentrations in drinking water may be reasonable from a regulatory perspective, advances in risk assessment and risk management will likely depend on knowledge of the individual arsenic species.

Speciation analysis of an element in water samples (Lund, Fres. J. Anal. Chem., 1990, 337, 557–564; Ure, Mikrochim. Acta, 1991, II, 49–57) involves the use of analytical methods that can provide information about the physicochemical forms of the element, which together make up its total concentration in the sample. The individual physicochemical forms may include particulate matter and dissolved forms such as simple organic species, organic complexes and the element adsorbed on a variety of colloidal particles (Florence, Analyst, 1986, III, 489–524). Schroeder (Trends Anal. Chem., 1989, 8, 339–342) distinguishes physical speciation, which involves differentiation of the physical size or the physical properties of the element, and chemical speciation, which refers to the differentiation among the various chemical forms. Thus, speciation can be defined as the occurrence of different forms, chemical and/or physical, of an element in the real samples.

The speciation of arsenic in the environment is of great significance due to the different toxicity levels exhibited by the various species present in environmental and clinical samples (WHO, Arsenic in Drinking Water, 2001, Vol. 2001; Jain, Water Res., 2000, 34, 4304–4312). The more common arsenic species are arsenate As(III), arsenate As(V), arsenious acids ($H_3SO_4$, $H_2AsO_4^-$, $HAsO_4^{2-}$), arsenic acids ($H_3AsO_4$, $H_2AsO_4^-$, $HAsO_4^{2-}$), dimethylarsinate (DMA), monomethylarsonate (MMA), arsenobetaine (AB) and arsenocholine (AC). These forms illustrate the various oxidation states that arsenic commonly exhibits (–III, 0, III, V) and the consequently complexity of its chemistry in the environment.

Arsenic contamination in natural water is a worldwide problem and has become a challenge for the world scientists. Arsenic speciation is important because As(III) is found to be more water soluble and more mobile in the environment (Woolson, In Topics in Environmental Health, Biological and Environmental Effects of Arsenic; Fowler, Ed.; Elsevier: New York, 1983; pp. 51–139). The degree of toxicity of arsenic species is inversely proportional to the rate of excretion from the body and can be shown as follows: arsine>As (III)>As (V)>MMA>DMA (Puttemans and Massart, Analytical Chimica Acta 1982, 141, 225; Russeva and Havezov, Bulgarian Chem. Comm., 1993, 26, 228–238). Data on the differences in toxicity between As(III) and As(V) on human beings are very limited.

In spite of the numerous analytical approaches for arsenic speciation in the last few years, there still remains the need for a sensitive method, which allows determining effectively, and simultaneously, the four most important arsenic species (As(III), As(V), MMA, and DMA) in different matrixes. The approaches that have been developed for speciation studies of arsenic have their own advantages and limitations. However, research efforts, are still needed to develop inexpensive, rapid, sensitive, and reproducible methodologies for arsenic species capable of working in the range of drinking water limits.

SUMMARY OF THE INVENTION

The present invention provides a method and test for field sample arsenic speciation in aqueous solutions, in particular, arsenic speciation in drinking water. In particular, the method and test uses in series three columns wherein the first column removes interfering cations from water, the second column removes dimethylarsenate (DMA) from the water, and the third column removes As(V) (collectively $H_3AsO_4/H_2AsO_4^-/HAsO_4^{2-}/AsO_4^{3-}$) and monomethylarsinate (MMA) while As(III) (collectively $H_3AsO_3/H_2AsO_3^-/HAsO_3^{2-}/AsO_3^{3-}$) remains in the water effluent. The bound arsenic species are separately eluted from the columns in a laboratory and then each of the eluants and the effluent are tested for the arsenic species, preferably using graphite furnace atomic absorption spectroscopy.

Therefore, the present invention provides a method of field sample collection for the detection of arsenic species As(III), As(V) monomethylarsonate (MMA), and dimethylarsinate (DMA) in drinking water which comprises (a) providing three separate solid phase extraction media for a serial extraction of the drinking water in the field wherein a first of the media removes interfering cation ions in the water from the As (V), MMA, DMA, and As(III) in the water; a second of the media at a pH of about 1.0 to 1.5 removes the DMA in the water from the As(V), MMA, and As(III) in the water; and a third of the media, which particular embodiments comproses dioctyltin dichloride, at a pH of 2.5 to 3.5 which removes the As(V) and MMA in the water from the As(III) in the water; and (b) serially introducing the water into the first, second, and third media, and collecting a first eluent from the third media containing the As(III).

The present invention further provides a method of field sample preparation of water samples to separate, for the purpose of subsequent chemical analysis, the arsenic species (i) arsenate/arsenous acid ($H_3AsO_3/H_2AsO_3^-/HAsO_3^{2-}/AsO_3^{3-}$ or collectively As(III)), (ii) arsenate/arsenic acids ($H_3AsO_4/H_2AsO_4^-/HASO_4^{2-}/AsO_4^{3-}$ or collectively As(V)), (iii) monomethylarsonic acid (($CH_3AsO(OH)_2$ or MMA), and (iv) dimethylarsinic acid (($CH_3)AsO(OH)$ or DMA) which comprises (a) providing three separate solid phase extraction columns for a serial extraction of the drinking water in the field wherein a first of the columns which is a cation exchange column comprising a medium for ion exchanging which removes interfering cation ions in the water from the As (V), MMA, DMA, and As(III) in the water; a second of the columns which is a cation exchange column comprising a medium at a pH of about 1.0 to 1.5 for ion exchanging which removes the DMA in the water from the As(V), MMA, and As(III) in the water; and a third of the columns which is an exchange/sorption column comprising a dioctyltin dichloride coated medium at a pH of 2.5 to 3.5 which removes the As(V) and MMA in the water from the As(III) in the water; and (b) serially introducing the water into the first, second, and third columns, and collecting a first eluent from the third column containing the As(III).

The present invention further provides a kit for collection of a field sample for the detection of arsenic species As(III), As (V), monomethylarsonate (MMA), and dimethylarsinate (DMA) in drinking water which comprises three separate solid phase extraction media wherein a first of the media removes interfering cation ions in the water from the AS(V), MMA, DMA, and As(III) in the water; a second of the media which at a pH of about 1.0 to 1.5 removes the DMA in the water from the AS(V), MMA, and As(III) in the water; and a third of the media comprising dioctyltin dichloride, preferably as a coating on diatomaceous earth, which at a pH of 2.5 to 3.5 removes the As(V) and MMA in the water from the AS(III) in the water.

The present invention further provides a kit for preparation of water samples to separate, for the purpose of subsequent chemical analysis, the arsenic species (i) arsenate/arsenous acid ($H_3AsO_3/H_2AsO_3^-/HAsO_3^{2-}/AsO_3^{3-}$ or collectively As(III)), (ii) arsenate/arsenic acids ($H_3AsO_4/H_2AsO_4^-/HASO_4^{2-}/AsO_4^{3-}$ or collectively As(V)), (iii) monomethylarsonic acid (($CH_3AsO(OH)_2$ or MMA), and (iv) dimethylarsinic acid (($CH_3)_2AsO(OH)$ or DMA) which comprises three separate solid phase extraction columns wherein a first of the columns which is a cation exchange column comprising a media for ion exchanging which removes interfering cation ions in the water from the As(V), MMA, DMA, and As(III) in the water; a second of the columns which is a cation exchange column comprising a media at a pH of about 1.0 to 1.5 for ion exchanging which removes the DMA in the water from the As(V), MMA, and As(III) in the water; and a third of the columns which is an exchange/sorption column comprising a dioctyltin dichloride coated media, preferably as a coating on silanized diatomaceous earth, at a pH of 2.5 to 3.5 which removes the As(V) and MMA in the water from the As(III) in the water.

In further embodiments of the above methods and kits, the first of the media is a weak acid cation exchange medium. In further still embodiments, the weak acid cation medium comprises a functional group selected from the group consisting of iminodiacetate, amino phosphonic, phosphinic, and methylene thiol immobilized thereon. In further still embodiments, the functional group is iminodiacetate. In further still embodiments, the medium comprises polystyrene divinylbenzene.

In further embodiments of the above methods and kits, the second of the media is a strong acid cation exchange medium. In further still embodiments, the strong acid cation medium comprises a sulphonate functional group. In further still embodiments, the second of the media comprises polystyrene divinylbenzene.

In further embodiments of the above methods and kits, the third of the media comprises calcined diatomaceous earth.

OBJECTS

Therefore, it is an object of the present invention to provide a method for collecting arsenic species from an aqueous source in the field for analysis in a laboratory which preserves the arsenic speciation found at the aqueous source.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

Arsenic (As) speciation has received significant attention during recent years since the toxic effects of arsenic are related to its oxidation state and the total arsenic concentration in environmental samples does not reflect the level of hazard of this element. It is becoming increasingly important that the concentrations of the various forms of arsenic need to be determined to provide a much clearer view of the risk associated with arsenic exposure in the environment. Therefore, the object of the present invention is to provide an optimized and a relatively simple, rapid, sensitive, accurate, and relatively inexpensive method for the speciation of the As(III), As(V), monomethylarsonic acid/monomethylarsonate (MMAA/MMA), and dimethylarsonic acid/dimethylarsinate (DMAA/DMA) using solid phase extraction cartridges in water samples.

The present invention provides a simple, field-deployable, arsenic-species separation method that can be easily coupled to laboratory analysis methods for the four species of primary interest. Such a method is useful in both routine monitoring and exposure assessment studies. The present invention uses solid-phase extraction materials (media) to selectively retain particular As species and a sequential extraction approach based on these materials to isolate all four As species. The method uses a simple three column cartridge system, the first and second columns each containing a particular cation exchange medium with particular exchange properties and the third column contains an exchange/sorption medium, that can be used in the field to collect the samples and make extracts of the samples followed by laboratory elution of the extracts and GFAAS analysis of the extracts to produce accurate and precise As species concentration data.

The first column cartridge contains a cation exchange medium which binds and removes interfering ions such as $Na^+$, $Ca^{++}$, $Mg^+$, and the like which may be present in an aqueous sample and which may destabilize one or more of the arsenic species. The effluent from the first column is acidified to a pH of about 1.0 to 1.5, which protonates the DMA and DMAA to a cationic form, and passed over the second column which contains a cation exchange medium which at the low pH binds the protonated DMA while allowing the other arsenic species (As(III), As(V), and MMA) to pass through. The DMA is stable while bound to the medium and can be eluted from the medium using 1 M HCl or 1 M $NH_4OH$. The effluent from the second column is pH adjusted to about 2.5 to 3.5 and passed over the third column which contains a medium which binds As(V) and MMA while allowing the As(III) to pass through. The As(V) and MMA are stable while bound to the medium and the As(III) in the effluent is stable because the interfering ions were removed by the medium in the first column.

The method enables on-site separation of the arsenic species without the storage and preservation problems which can be caused by interfering ions in the sample, oxidation of various arsenic species, and so forth. In other words, the method stabilizes the arsenic species which might be present in a sample from an aqueous source. Because the arsenic species are stabilized, the amounts of the arsenic species in the sample which are determined by laboratory analysis correspond to the amounts of the arsenic species which are actually present at the aqueous source. The amounts of each arsenic species in an aqueous source provides important information as to the arsenic toxicity of the aqueous source. For example, As(III) can be oxidized to As(V) during storage and transport of a water sample to a laboratory for analysis. While As(III) and As(V) are both toxic, As(III) is about 25 to 60 times as toxic as As(V). Oxidation of As(III) to As(V) during storage and transport of a sample will produce a result during analysis which would make it appear that the arsenic level in the aqueous source is less toxic than it really is. However, because the present invention stabilizes the arsenic species for storage and transport, the amounts of the arsenic species detected during analysis more accurately reflect the amounts that are present in the aqueous source.

Figure 1:
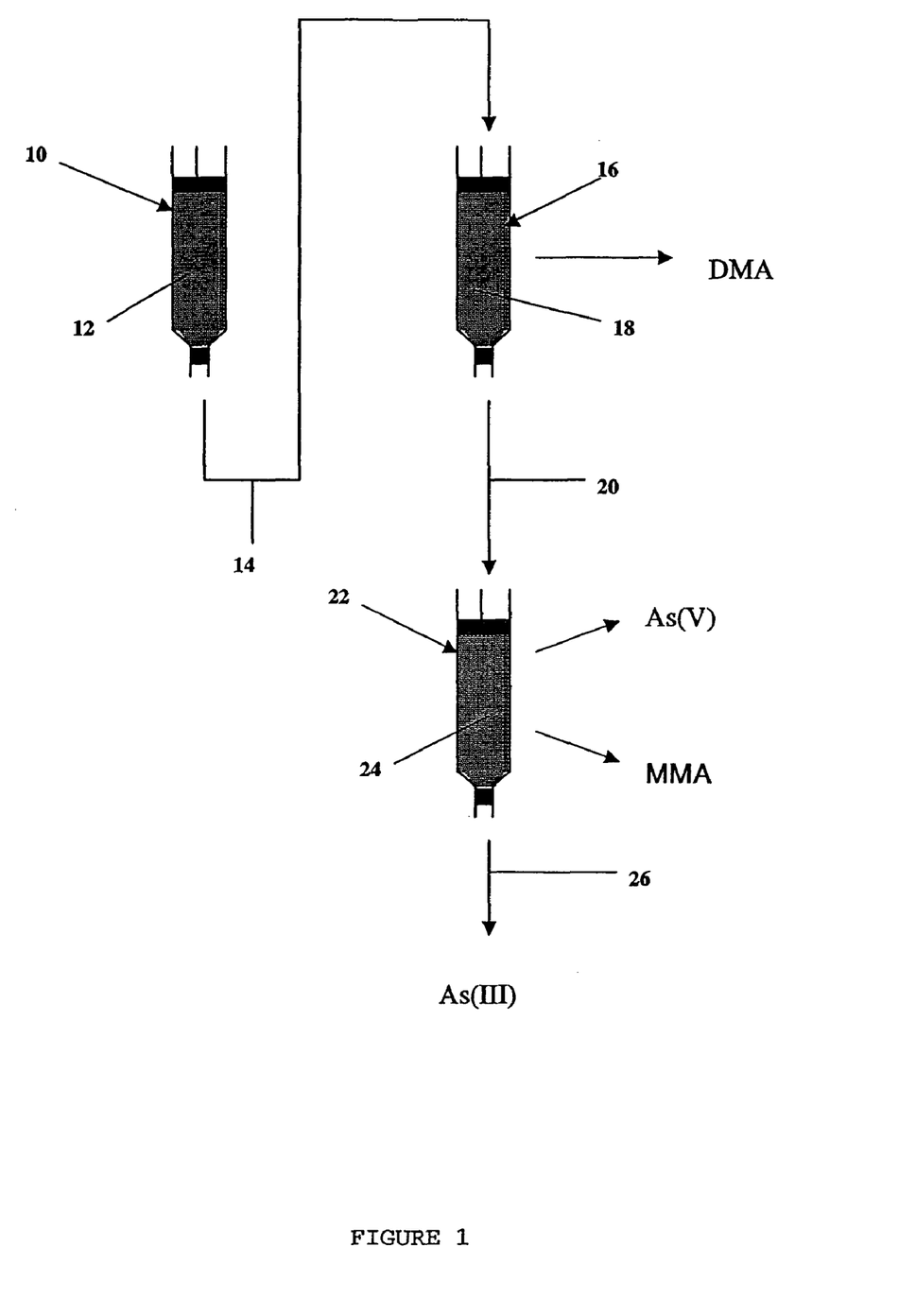
FIG. 1 illustrates the method of the present invention.

In a first embodiment of the present invention, the method uses a set of three column cartridges and a selective elution procedure. This embodiment is also illustrated in FIG. 1.

The first column cartridge 10 contains a first cation exchange medium 12 to remove interfering cations. The interfering cations are bound to the first cation medium 12 while the various arsenic species are not bound and remain in the effluent 14. The pH of the effluent 14 is then reduced to about pH 1 to 1.5, which results in formation of the protonated cation of DMA. The DMA is then extracted from the effluent 14 with a second column cartridge 16 containing a second cation exchange medium 18. The DMA is stable while bound to the second cation exchange medium 18 and can be transported while bound to the second cation exchange medium 18 in the second column cartridge 16 to a laboratory for quantitative analysis. In the laboratory, the DMA is eluted from the second cation exchange medium 18 with an acid or a base (for example, when the second cation medium 18 is a strong acid cation exchanger, 1 M HCl or 1 M $NH_4OH$ can be used to elute the DMA). Meanwhile, the pH of the effluent 20 is increased to a pH of about 2.5 to 3.5. The As(V) and MMA are then extracted from the effluent 20 with a third column cartridge 22 containing an exchange/sorption medium 24 comprising silanized diatomaceous earth coated with dioctyltin dichloride. The As(V) and MMA are stable while bound to the exchange/sorption medium 24 and can be transported while bound to the exchange/sorption medium 24 to a laboratory for quantitative analysis. In the laboratory, the As(V) and MMA are separately eluted from the exchange/sorption medium 24 with different strength acids (for example, As(V) can be eluted with 0.2 M HCl and MMA can be eluted with 1 M HCl). The As(III), which is not bound by the exchange/sorption medium 24 is stable in the effluent 26.

In general, water samples or effluents are delivered to the set of three cartridges 10, 16, 24 and passed through the cartridges using either centrifugation, syringes, vacuum manifolds, peristaltic pumps, or any other means which will pull the water sample or effluent through the cartridge. In further embodiments, the cartridges can be components of an apparatus in which the method of the present invention is automated. Thus, the method of the present invention provides a means for stabilizing arsenic species distribution in a sample for transport to a laboratory for quantitative analysis.

The mechanism for the separation of As(V), MMA, and As(III) on the exchange/sorption medium has not been established but it appears to be based on the reaction of exchange of chloride ion that is present in the dioctyltin dichloride molecule with the $H_2AsO_4^-$ ion. The As(V) anion has very high affinities for the dioctyltin cation because of the stronger tin-oxygen bonds of the anion (Davies, Organotin Chemistry; VCH: New York, 1997; Shkinev et al., Anal. Chim. Acta, 1985, 167, 145–160; Spivakov, et al., J. Appl. Chem. USSR, 1983, 716–720) and the pH of the extracting solution is in the range 2.5–3.5 where $H_2AsO_4^-$ ion is the only ion present. Thus, the mechanism for these separations is believed to be that As(V) is retained as $H_2AsO_4^-$ by a combination of anion exchange with the formation of tin-oxygen bonds, while MMA is held by the diatomaceous earth. As(III) is found in the effluent as it remains in the neutral form and is not retained.

The first solid phase extraction medium is preferably a weak acid cation exchange medium (or resin) which comprises a medium having immobilized or covalently bound thereon weak acid cation exchange functional groups. Weak acid cation exchange functional groups are in general groups comprising carboxyl groups. Examples of weak acid cation exchange functional groups include iminodiacetate, amino phosphonic, phosphinic, phenolic, selenoic, and methylene thiol. The media comprises powder, particles, beads, or gel fabricated from any suitable matrix or support material such as a polystyrene copolymer or other polymer, agarose, polymethacrylate, silica, or the like. Preferably, the particles or beads comprising the media have substantial porosity with a large surface area. In particular embodiments, the media support material comprises a resin such as polystyrene divinylbenzene in a cross-linking ratio between about 1 to 10%, preferably between 4 and 8%, to which the functional groups are immobilized or covalently bound. An example of a suitable weak acid cation exchange medium is CHELEX-100 or a derivative or variant thereof (CHELEX is a trademark of Bio-Rad Laboratories, Inc., Hercules, Calif.). Preferably, the weak acid cation exchange medium is provided in its sodium form. The medium is mixed with deionized water to swell or hydrate the resin and optionally, then packed into columns. The medium is then converted to the ammonia form by mixing it with a solution containing ammonium hydroxide (for example, 1 M $NH_4OH$) or if in a column, passing the ammonium hydroxide solution through the column. Afterwards, the medium is washed with deionized water to remove the ammonium hydroxide. The media in its ammonia form is suitable for removing interfering cations in an aqueous sample. The media can be stored in a sealed column or in bulk in a sealed container in a dry or hydrated form until ready for use. For example, the media can be stored in a hydrated form in deionized water or an ammonium hydroxide solution. The ammonium hydroxide is removed prior to use by washing the media with deionized water to remove the ammonium hydroxide.

The second solid phase extraction medium is preferably a strong acid cation exchange medium (or resin) which comprises a medium having immobilized or covalently bound thereon strong acid cation exchange functional groups. Strong acid cation exchange functional groups are groups such as sulphonate groups. The media comprises powder, particles, beads, or gel fabricated from any suitable matrix or support material such as a polystyrene copolymer or other polymer, agarose, polymethacrylate, silica, or the like. Preferably, the particles or beads comprising the media have substantial porosity with a large surface area. In particular embodiments, the media support material comprises a resin such as polystyrene divinylbenzene in a cross-linking ratio between about 1 to 10%, preferably between 4 and 8%, to which the functional groups are immobilized or covalently bound. An example of a suitable strong acid cation exchange media is DOWEX 50w or a derivative or variant thereof (DOWEX is a trademark of Dow Chemical Company, Midland, Mich.). Preferably, the strong acid cation exchange medium is provided in the hydrogen form, which is mixed with water to swell or hydrate the media. Optionally, the resin is packed into a column. Afterwards, the medium is mixed with an acid solution such as 0.1 M HCl. Alternatively, the medium is allowed to swell or hydrate in the acid solution. The media can be stored in a sealed column or in bulk in a sealed container dry or in a hydrated form such as in the acid solution until ready for use.

The third solid phase extraction medium preferably comprises a calcined diatomaceous earth or silica particular support material with dioctyltin dichloride immobilized thereon. An example of a suitable support is the calcined diatomaceous earth available as CHROMOSORB W or derivative or variant thereof (CHROMOSORB is a trademark of Celite Corporation, Lompoz, Calif.). To prepare the medium, dioctyl tin dichloride is dissolved in n-decanol and mixed with chloroform as a carrier solvent. The mixture is mixed with the calcined diatomaceous earth or silica support for a time sufficient to bind the dioctyl tin dichloride to the support. After drying, the medium is mixed with an acid solution such as 0.001 M HCl for packing into columns. The media can be stored in a sealed column or in bulk in a sealed container in a hydrated form in the acid solution until ready for use. Alternatively, the media can be stored in its dry form.

It is convenient to provide the above media (or resin) in cartridge-type columns (FIG. 1) such as those which can be mounted on a syringe for development of the column by pressure or as spin columns wherein the development is effected by centrifugation. Cartridge and spin column formats are well known in the art. The requirement for the columns in either format is that the inlet and outlet ends of the column be sealably closable to prevent loss or drying of the media. For example, the end of each inlet and outlet can be threaded to receive a screw cap or push caps can be provided to cover the end of each inlet and outlet. The columns further require a support means at the opposite end to prevent the media from exiting through the outlet during use. The support means can be any means which prevents the media from exiting the column while allowing the water and effluents to flow through the column. Support means include paper, cellulose, nitrocellulose, polymer membrane, fritted glass, glass wool, or the like.

However, the method of the present invention includes embodiments other than column-based methods as well. For example, the method can be performed using a batch method wherein the first solid phase exchange medium is prepared as described above and then mixed with the sample in a centrifuge or microfuge tube. The first solid phase extraction medium is then formed into a pellet by centrifugation and the supernatant fraction is removed, acidified to about pH 1 to 1.5, and mixed with the second solid phase extraction medium prepared as described above. The first solid phase extraction medium pellet can be discarded. The second solid phase extraction medium is then formed into a pellet by centrifugation and the pellet containing the DMA is saved for elution of the DMA for laboratory analysis. The pH of the supernatant fraction is adjusted to a pH of about 2.5 to 3.5 and then mixed with the third solid phase extraction medium prepared as described above. The third solid phase extraction medium is then formed into a pellet by centrifugation and the pellet containing the As(V) and MMA is saved for elution of the As(V) and MMA for laboratory analysis. The supernatant fraction containing the As(III) is also saved for laboratory analysis. In some instances, to maximize recovery of the arsenic species, the pellets are resuspended in the appropriate solution, centrifuged, and the supernatant fractions combined with the appropriate supernatant fraction. In lieu of centrifugation, the above mixtures can be passed through a syringe-mounted filter of suitable porosity to retain the medium.

The present invention further provides kits which provide the first cation medium, the second cation medium, and the third exchange/sorption medium. In particular embodiments of the kit, the media are provided in separate closed containers containing the media in dry form, in a wet or hydrated form, or mixtures wherein one or more of the media are in wet form and the remaining media are in dry form. In other embodiments of the kit, the kit provides the media packed into a plurality of separate columns, cartridge columns, or the like, comprising glass or a polymer. Each of the columns has an inlet end for applying the aqueous sample and an outlet end for recovering the effluent or eluant. The inlets and outlets are sealably closable to prevent loss or drying of the media. For example, the end of each inlet and outlet can be threaded to receive a screw cap or push caps can be provided to cover the end of each inlet and outlet. The media can be in dry or wet or hydrated form. The separate columns can be spin-columns or cartridge-type columns. The columns further comprise a support means at the opposite end to prevent the media from exiting through the outlet during use. The support means can comprise paper, cellulose, nitrocellulose, polymer membrane, fritted glass, glass wool, or any other support means which prevents the media from exiting the column while allowing the water and effluents to flow through column.

The following examples are intended to promote a further understanding of the present invention.

EXAMPLE 1

This example illustrates the concept of the present invention. In this example, selective retention of arsenic species on specific solid phase extraction cartridges is followed by selective elution and quantification using graphite furnace atomic absorption spectroscopy (GFAAS).

In general, a set of ten replicate spiked samples of each compound, having concentrations between 1 to 60 µg/L, were analyzed. Arsenic recoveries ranged from 78–112% and relative standard deviations were generally below 10%. Resolution between species was shown to be outstanding, with the only limitation being that the capacity for As(V) was limited to approximately 50 µg/L. This could be easily remedied by changes in either cartridge design or the extraction procedure. Recoveries were similar for two spiked hard groundwater samples indicating that dissolved minerals are not likely to be problematic. These results in this example show that the present invention can be use for analysis of the four primary arsenic species of concern in drinking water supplies.

Cartridges were prepared using a slurry method. A small plug of glass wool was placed in the bottom of the cartridges to provide a support for the media. A small volume of an appropriate solvent was mixed with the extraction media to form a homogeneous paste that would flow. This paste was poured into the cartridges, taking care to prevent cracks, channels and air bubbles. Glass wool was placed on the top to hold the media in place. Three cartridges were used, the first removes interferences; the second one retained DMA and third retains As(V) and MMA.

Cartridge 1 was packed with 0.6 g CHELEX 100 in sodium form, as purchased, using deionized water as a solvent. It was then converted to the ammonia form by passing 20 mL of 1.0 M $NH_4OH$ through the cartridge. The cartridge was then flushed with about 50 mL deionized water to remove the residual $NH_4OH$. CHELEX 100 is available from Bio-Rad Laboratories, Inc., Hercules, Calif. A plastic cartridge was used.

Cartridge 2 was packed with 0.3 g DOWEX 50w (50–100 mesh, 8% cross-linkage) in the hydrogen form as purchased using 0.1 M HCl as a solvent. DOWEX 50w is available from Dow Chemical Company, Midland, Mich. A plastic cartridge was used.

Cartridge 3 was packed with a custom sorbent prepared as follows. Dioctyl tin dichloride was dissolved in n-decanol and mixed with chloroform as a carrier solvent. This solution was shaken with CHROMOSORB W for 2 hours and dried at room temperature. CHROMOSORB W is available from Celite Corporation, Lumpoc, Calif. The suspension was dried using a rotary evaporator at room temperature, and the dry material is used to pack glass cartridges using 0.001 M HCl as a solvent.

After initial development of the procedure, optimization studies were performed to evaluate the effects of variations in pH adjustment between cartridges, and flow rates for both extraction and elution. The capacities of cartridges 2 and 3 were evaluated for the three species retained. The optimized extraction/elution procedure is shown schematically in FIG. 1. A water sample was first passed through cartridge 1 using either a syringe or peristaltic pump. The effluent was adjusted to pH 1–1.5 with 1M HCl and passed through Cartridge 2 at a rate of 3–4 mL/min. The effluent was adjusted to pH 2.5–3.5 using $NH_4OH$ and passed through Cartridge 3 at a rate of 0.5–1 mL/min. Cartridge 2 was eluted with 5 mL 1 M HCl to produce the DMA fraction. Cartridge 3 was first eluted with 8 mL 0.2 M HCl and then with 5 mL of 1.0 M HCl to produce As(V) and MMA fractions, respectively. The effluent of Cartridge 3 contained the As(III) fraction.

An arsenate standard solution (Inorganic Ventures, Inc.) containing 100.00 µg as As/mL in 0.7% perchloric acid was used as the As (V) stock solution and as an analytical standard. An As(III) stock solution was prepared by dissolving high purity arseniuos oxide (GFS Chemical) in a minimal volume of 1 M NaOH, neutralizing with 1 M HCl using a methyl orange indicator, and diluting with dionized water to achieve a concentration of 1,000 mg as As/L. Stock solutions containing 1,000 mg as As/L of monomethyl arsonate (Chem Service) and dimethyl arsinate (GFS Chemical) were prepared by direct dissolution in dionized water. Standard solutions, which were used for the calibration and spiked samples were prepared daily by dilution of the stock solutions. All chemicals were trace analysis grade.

The four fractions were analyzed using graphite furnace atomic absorption spectroscopy (GFAAS). A matrix modifier solution containing palladium chloride, bi-distilled hydrochloric acid, ammonium para-tungstate, and citric acid was employed. An electrodeless discharge lamp (EDL) was used with Zeeman-effect background correction. Ultra-clean graphite tubes with integrated platforms tube were with the furnace temperature program shown in Table 1.

TABLE 1

Furnace Temperature Program For As Analysis

| Step | Temp (° C.) | Ramp (s) | Hold (s) | Read | Flow (mL/min) |
|---|---|---|---|---|---|
| 1 | 110 | 1 | 30 | | 250 |
| 2 | 130 | 15 | 30 | | 250 |
| 3 | 1200 | 10 | 20 | | 250 |
| 4 | 2000 | 0 | 5 | x | 0 |
| 5 | 2400 | 1 | 3 | | 250 |

To evaluate the method, water samples were spiked with various concentrations and combinations of the four arsenic species by adding the appropriate stock solution to water and immediately passing the solution through the series of cartridges. Solutions containing the four compounds individually were analyzed over the concentration range 10–100 µg as As/L. Ten replicates of twelve different combinations of the four species at levels up to 100 µg as total As were also analyzed. Finally, a comparison between spiked samples using deionized water and very hard groundwater was performed.

Results and Discussion

Seven-point calibration curves for the each of the four arsenic species were established for the concentration range of 1 to 10 µg/L and 5 to 100 µg/L using peak areas. Correlation coefficients were higher than 0.998 for all species and the relative standard deviations for the points of the calibration graphs were between 5–10% for 1–10 ppb and 1–6% from 5–100 µg/L. Previous studies have reported different response factors, or slopes of the calibration curves, for different As species (Masscheleyn et al.,. Environ. Sci. Technol., 1991, 20, 96–100; Ochsenkuhn-Petropolu et al., Canadian J. Appl. Spectro., 1995, 40, 61–65). We found no significant differences. Three replicates of the calibration procedure were performed on each of three different days. The relative standard deviation did not exceed 8% for 1–10 µg/L and 5% for the concentration range of 5–100 µg/L. A detection limit of 0.37 µg/L was determined using the criterion 3×σ/S, where σ is the standard deviation of the ten replicates of background signal and S is the slope of the calibration curve (IUPAC Pure and Applied Chemistry, 1995, 67, 1699–1723; Jaganathan, Atomic Spectrometry, 2001, 22, 280–283).

Figure 2:
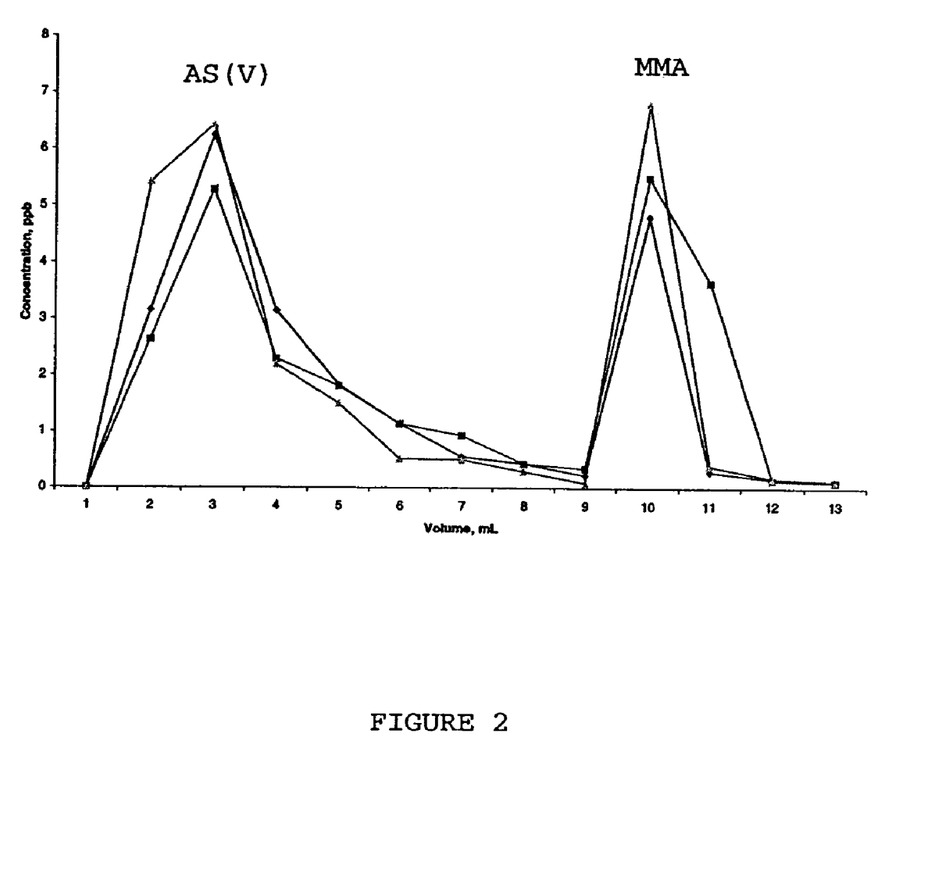
FIG. 2 shows the elution curves for As (V) and MMA separation. ■ is a first run; Δ is a second run; and ♦ is a third run.

Optimization studies for extraction pH indicated that complete retention of DMA occurred in the pH range 1.0–1.5. Similarly, complete retention of As (V) and MMA was achieved in the pH range 2.5–3.5. The effect of the flow rate for extraction by cartridges 2 and 3 was evaluated over the range 0.5–4 mL/min using peristaltic pumps in place of syringes that would normally be employed under field conditions. The best results were obtained in the range 3–4 mL/min for cartridge 2 and 0.5–1 mL/min for cartridge 3. Elution flow rate was evaluated over the same range with the result that 0.5–1 mL/min was best for cartridge 2 and 1 mL/min for cartridge 3. The elution curve for cartridge 3 shown in FIG. 2 demonstrates excellent resolution of As (V) and MMA.

Table 2 shows the results obtained using deionized water spiked with each of the four arsenic species individually at concentrations from 10 to 100 µg/L. It can be seen that in all cases except for the higher levels of As (V), recovery is essentially complete (98–102%). Recovery of As (V) drops to 82% and 67% in the 80 and 100 µg/L samples, respectively. An amount of As similar to that not recovered appears as a "false positive" amount of As (III). This suggests that the capacity of cartridge 3 for As (V) is between 50 and 80 µg/L (1.25–2 µg) such that the As (V) introduced to the column above this amount is not retained, and appears in the column effluent, which is where we would expect to find As (III). This could be easily addressed by using a smaller volume of sample, or in future designs, by either using more sorbent material or higher loading of dioctyltindichloride on the sorbent.

TABLE 2

| | Interference Among Four Arsenic Species (concentration in µg/L) | | | |
|---|---|---|---|---|
| | As (III) | As (V) | MMA | DMA |
| Spiked | 10 | — | — | — |
| % recovery | 99.5 | | | |
| % S.D. | 6.4 | | | |
| Spiked | 50 | — | — | — |
| % recovery | 98.6 | | | |
| % S.D. | 1.4 | | | |
| Spiked | 80 | | | |
| % recovery | 100.9 | | | |
| % S.D. | 1.8 | | | |
| Spiked | 100 | | | |
| % recovery | 101.9 | | | |
| % S.D. | 2.5 | | | |
| Spiked | — | 10 | — | |
| % recovery | | 102.5 | | |
| % S.D. | | 6.1 | | |
| Spiked | — | 50 | — | |
| % recovery | 1.83 | 98.16 | | |
| S.D. | 5.4 | 2.4 | | |
| Spiked | — | 80 | | |
| % recovery | 15.8 | 81.7 | | |
| % S.D. | 4.8 | 2.6 | | |
| Spiked | — | 100 | | |
| % recovery | 39.5 | 67 | | |
| % S.D. | 2.7 | 1.8 | | |
| Spiked | — | — | 10 | — |
| % recovery | 1.9 | | 98.0 | |
| % S.D. | 3.4 | | 6.0 | |
| Spiked | | | 50 | |
| % recovery | | | 100.1 | |
| % S.D. | | | 3.4 | |
| Spiked | | — | 80 | |
| % recovery | 1.8 | | 98.7 | |
| % S.D. | 2.4 | | 2.2 | |
| Spiked | — | | 100 | |
| % recovery | 0.76 | | 100.4 | |
| % S.D. | 6.8 | | 1.5 | |

TABLE 2-continued

| | Interference Among Four Arsenic Species (concentration in µg/L) | | | |
|---|---|---|---|---|
| | As (III) | As (V) | MMA | DMA |
| Spiked | | | | 10 |
| % recovery | 1.7 | | | 98.5 |
| % S.D. | 5.6 | | | 4.9 |
| Spiked | | | | 50 |
| % recovery | | | | 103.3 |
| % S.D. | | | | 1.1 |
| Spiked | | | | 80 |
| % recovery | 0.96 | | | 98.9 |
| % S.D. | 5.6 | | | 2.4 |
| Spiked | | | | 100 |
| % recovery | 2.4 | | | 97.9 |
| % S.D. | 4.5 | | | 1.9 |

It was of interest to evaluate whether the cartridges could be reused after elution. Cartridges 1 and 2 used commercial materials designed to be regenerated so reuse of these cartridges were not tested further. However, cartridge 3 was tested for the ability to be reused after elution. Cartridge 3 was subjected to 50 extraction/elution cycles. Analytical performance remained constant over this period of use. The stability of extracted materials on the cartridge 3 was also evaluated by comparison of eluants from cartridges eluted immediately to eluants from cartridges eluted after one month of storage at room temperature covered with aluminum foil. No differences in stability were found.

The performance of the method of the present invention for samples containing multiple As species is shown in Table 3. Ten replicates of various combinations and concentrations of the four species ranging from 1 to 60 µg/L were prepared in deionized water. It can be seen from the results that recoveries were all greater than 80%. Precision was very good with relative standard deviations in general less than 5% except for when concentrations were less than 10 µg/L, in which case slightly higher values were found.

Two groundwater samples with different hardness levels were spiked with different concentrations of the four arsenic species to evaluate whether the presence of other ions that would normally be present affect recovery. The results from five replicates of each water sample are shown in Table 4. It can be seen that acceptable recoveries and comparable precision was found for the groundwater samples.

TABLE 3

| | As (III) | As (V) | MMA | DMA |
|---|---|---|---|---|
| Spiked (µg/L) | 0 | 40 | 10 | 0 |
| % recovery | | 86.45 | 92.34 | |
| % RSD* | | 1.2 | 2.1 | |
| Spiked (µg/L) | 0 | 40 | 10 | 10 |
| % recovery | | 89.45 | 94.35 | 105.45 |
| % RSD | | 1.8 | 4.9 | 6.4 |
| Spiked (µg/L) | 40 | 40 | 10 | 10 |
| % recovery | 98.56 | 84.89 | 93.56 | 101.45 |
| % RSD | 2.0 | 1.4 | 3.8 | 5.2 |
| Spiked (µg/L) | 40 | 0 | 10 | 10 |
| % recovery | 112.34 | | 98.89 | 99.78 |
| % RSD | 2.1 | | 3.8 | 2.9 |
| Spiked (µg/L) | 40 | 40 | 10 | 0 |
| % recovery | 108.32 | 90.45 | 110.23 | |
| % RSD | 2.1 | 1.9 | 4.6 | |
| Spiked (µg/L) | 40 | 20 | 0 | 0 |
| % recovery | 97.34 | 83.57 | | |
| % RSD | 3.9 | 2.6 | | |
| Spiked (µg/L) | 40 | 40 | 0 | 10 |

TABLE 3-continued

|  | As (III) | As (V) | MMA | DMA |
|---|---|---|---|---|
| % recovery | 106.34 | 82.45 |  | 95.64 |
| % RSD | 3.0 | 2.1 |  | 5.3 |
| Spiked (µg/L) | 5 | 5 | 1 | 1 |
| % recovery | 87.45 | 78.68 | 0.86 | 108.25 |
| % RSD | 9.1 | 9.4 | 11.3 | 10.6 |
| Spiked (µg/L) | 20 | 10 | 5 | 5 |
| % recovery | 91.32 | 77.45 | 92.6 | 96.74 |
| % RSD | 3.7 | 6.7 | 6.9 | 6.6 |
| Spiked (µg/L) | 60 | 30 | 5 | 5 |
| % recovery | 93.83 | 84.42 | 93.42 | 97.50 |
| % RSD | 1.3 | 4.4 | 5.4 | 5.1 |
| Spiked (µg/L) | 30 | 60 | 5 | 5 |
| % recovery | 91.50 | 84.43 | 89.95 | 102.35 |
| % RSD | 3.5 | 6.4 | 7.4 | 5.6 |
| Spiked (µg/L) | 60 | 40 | 0 | 0 |
| % recovery | 90.34 | 88.54 |  |  |
| % RSD | 3.6 | 4.5 |  |  |

TABLE 4

Results of the Arsenic Speciation in Groundwater Samples

| Sample | Total Hardness as $CaCO_3$ (mg/L) | As (III) | As (V) | MMA | DMA |
|---|---|---|---|---|---|
| Well | 250 | 0.22 | 0.67 |  |  |
| Spiked (µg/mL) |  | 50 | 30 | 10 | 10 |
| % recovery |  |  | 86.85 | 97.42 | 105.23 |
| % RSD |  |  | 2.4 | 5.1 | 6.4 |
| MSU tapwater | 450 | 0.3 | 1.9 |  |  |
| Spiked (µg/mL) |  | 50 | 30 | 10 | 10 |
| % recovery |  |  | 95.45 | 84.35 | 98.87 | 101.45 |
| % RSD |  |  | 1.6 | 2.2 | 7.2 | 8.2 |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method of field sample collection for the detection of arsenic species As(III), As(V) monomethylarsinate (MMA), and dimethylarsinate (DMA) in drinking water which comprises:
    (a) providing three separate solid-phase extraction columns for a serial extraction of the drinking water in the field wherein
    (1) a first of the columns which is a cation exchange column comprising a first medium for ion exchanging which removes interfering cation ions in the water from the As(V), MMA, DMA, and As(III) in the water;
    (2) a second of the columns which is a cation exchange column comprising a second medium at a pH of about 1.0 to 1.5 for ion exchanging which removes the DMA in the water from the As(V), MMA, and As(III) in the water; and
    (3) a third of the columns which is an exchange/sorption column comprising a dioctyltin dichloride coated medium at a pH of 2.5 to 3.5 which removes the As(V) and MMA from the water while the As(III) remains in the water; and
    (b) serially introducing the water into the first, second, and third columns, and collecting a first effluent from the third column containing the As(III).

2. The method of claim 1 wherein the first medium for the first of the columns is a weak acid cation exchange media.

3. The method of claim 2 wherein the weak acid cation medium comprises a functional group selected from the group consisting of iminodiacetate, amino phosphonic, phosphinic, and methylene thiol.

4. The method of claim 3 wherein the functional group is iminodiacetate.

5. The method of claim 2, 3, or 4 wherein the first medium comprises polystyrene divinylbenzene.

6. The method of claim 1 wherein the second medium for the second of the columns is a strong acid cation exchange medium.

7. The method of claim 6 wherein the strong acid cation medium comprises a sulphonate functional group.

8. The method of claim 6 or 7 wherein the second medium comprises polystyrene divinylbenzene.

9. The method of claim 1 wherein the third medium comprises calcined diatomaceous earth.

10. A kit for collection of a field sample for the detection of arsenic species As(III), As(V), monomethylarsinate (MMA), and dimethylarsinate (DMA) in drinking water which comprises:
    three separate solid-phase extraction columns wherein
    (1) a first of the columns which is a cation exchange column comprising a first medium for ion exchanging which removes interfering cation ions in the water from the As(V), MMA, DMA, and As(III) in the water;
    (2) a second of the columns which is a cation exchange column comprising a second medium at a pH of about 1.0 to 1.5 for ion exchanging which removes the DMA in the water from the As(V), MMA, and As(III) in the water; and
    (3) a third of the columns which is an exchange/sorption column comprising a dioctyltin dichloride coated third medium at a pH of 2.5 to 3.5 which removes the As(V) and MMA in the water while the As(III) remains in the water.

11. The kit of claim 10 wherein the first medium of the first of the columns is a weak acid cation exchange media.

12. The kit of claim 11 wherein the weak acid cation medium comprises a functional group selected from the group consisting of iminodiacetate, amino phosphonic, phosphinic, and methylene thiol immobilized thereon.

13. The kit of claim 12 wherein the functional group is iminodiacetate.

14. The kit of claim 11, 12, or 13 wherein the first medium comprises polystyrene divinylbenzene.

15. The kit of claim 10 wherein the second medium of the second of the columns is a strong acid cation exchange media.

16. The kit of claim 15 wherein the strong acid cation medium comprises a sulphonate functional group.

17. The kit of claim 15 or 16 wherein the second medium comprises polystyrene divinylbenzene.

18. The kit of claim 10 wherein the third medium of the third column comprises calcined diatomaceous earth.

19. A method of field sample collection for the detection of arsenic species As(III), As(V) monomethylarsinate (MMA), and dimethylarsinate (DMA) in drinking water which comprises:
    (a) providing three separate solid-phase extraction media for a serial extraction of the drinking water in the field wherein
    (1) a first of the media removes interfering cation ions in the water from the As(V), MMA, DMA, and As(III) in the water;

(2) a second of the media at a pH of about 1.0 to 1.5 removes the DMA in the water from the As(V), MMA, and As(III) in the water; and (3) a third of the media which is coated at a pH of 2.5 to 3.5 removes the As(V) and MMA in the water while the As(III) remains in the water; and (b) serially introducing the water into the first, second, and third media, and collecting a first effluent from the third media containing the As(III).

20. The method of claim 19 wherein the first of the media is a weak acid cation exchange medium.

21. The method of claim 20 wherein the weak acid cation medium comprises a functional group selected from the group consisting of iminodiacetate, amino phosphonic, phosphinic, and methylene thiol.

22. The method of claim 21 wherein the functional group is iminodiacetate.

23. The method of claim 20, 21, or 22 wherein the first of the media comprises polystyrene divinylbenzene.

24. The method of claim 19 wherein the second of the media is a strong acid cation exchange medium.

25. The method of claim 24 wherein the strong acid cation medium comprises a sulphonate functional group.

26. The method of claim 24 or 25 wherein the second of the media comprises polystyrene divinylbenzene.

27. The method of claim 19 wherein the third of the media comprises calcined diatomaceous earth coated with dioctyltidichloride.

28. A kit for collection of a field sample for the detection of arsenic species As(III), As(V), monomethylarsonate (MMA), and dimethylarsinate (DMA) in drinking water which comprises:

three separate solid-phase extraction media in columns wherein (1) a first of the media in a first of the columns removes interfering cation ions in the water from the As(V), MMA, DMA, and As(III) in the water;

(2) a second of the media in a second of the columns which at a pH of about 1.0 to 1.5 removes the DMA in the water from the As(V), MMA, and As(III) in the water; and (3) a third of the media in a third of the columns which at a pH of 2.5 to 3.5 removes the As(V) and MMA in the water while 15 the As(III) remains in the water.

29. The kit of claim 28 wherein the first of the media is a weak acid cation exchange medium.

30. The kit of claim 29 wherein the weak acid cation medium comprises a functional group selected from the group consisting of iminodiacetate, amino phosphonic, phosphinic, and methylene thiol immobilized thereon.

31. The kit of claim 30 wherein the functional group is iminodiacetate.

32. The kit of claim 29, 30, or 31 wherein the first of the media comprises polystyrene divinylbenzene.

33. The kit of claim 28 wherein the second of the media is a strong acid cation exchange medium.

34. The kit of claim 15 wherein the strong acid cation medium comprises a sulphonate functional group.

35. The kit of claim 33 or 34 wherein the second of the media comprises polystyrene divinylbenzene.

36. The kit of claim 28 wherein the third of the media comprises dioctyltin dichloride coated calcined diatomaceous earth.

* * * * *

UNITED STATES PATENT AND TRADEMARK OFFICE
CERTIFICATE OF CORRECTION

| | | |
|---|---|---|
| PATENT NO. | : 7,153,698 B2 | |
| APPLICATION NO. | : 10/616138 | |
| DATED | : December 26, 2006 | |
| INVENTOR(S) | : Thomas C. Voice et al. | |

It is certified that error appears in the above-identified patent and that said Letters Patent is hereby corrected as shown below:

Column 1, line 35, "$H_2AsO_3^{2-}$" should be --$H_2AsO_3^-$--.

Column 17, line 27-28, "dioctyltidichloride" should be -- dioctyltin dichloride--.

Column 18, line 11, "while 15 the As (III)" should be --while the As (III) --.

Signed and Sealed this

Fourth Day of September, 2007

JON W. DUDAS
*Director of the United States Patent and Trademark Office*